United States Patent
Mueller et al.

(10) Patent No.: US 11,234,793 B2
(45) Date of Patent: Feb. 1, 2022

(54) FILM CLAMPING ELEMENT

(71) Applicant: Ivoclar Vivadent AG, Schaan (LI)

(72) Inventors: Frank Mueller, Feldkirch (AT); Lukas Enggist, Sargans (CH)

(73) Assignee: Ivoclar Vivadent AG, Schaan (LI)

( * ) Notice: Subject to any disclaimer, the term of this patent is extended or adjusted under 35 U.S.C. 154(b) by 37 days.

(21) Appl. No.: 16/680,763

(22) Filed: Nov. 12, 2019

(65) Prior Publication Data
US 2020/0188060 A1     Jun. 18, 2020

(30) Foreign Application Priority Data
Dec. 12, 2018  (EP) .................................... 18212089

(51) Int. Cl.
| | | |
|---|---|---|
| *A61B 1/32* | (2006.01) | |
| *A61C 5/90* | (2017.01) | |
| *A61B 1/24* | (2006.01) | |

(52) U.S. Cl.
CPC .................. *A61C 5/90* (2017.02); *A61B 1/24* (2013.01); *A61B 1/32* (2013.01)

(58) Field of Classification Search
CPC .... A61C 5/80; A61C 5/82; A61C 5/90; A61B 1/32; A61B 17/02; A61B 17/0218; A61B 17/3421; A61B 17/3423; A61B 17/3431; A61B 2017/0225; A61B 2017/3429; A61B 2017/3443; A61B 1/24
See application file for complete search history.

(56) References Cited

U.S. PATENT DOCUMENTS

| | | | |
|---|---|---|---|
| 7,988,626 B2 | 8/2011 | Horvath | |
| 8,459,993 B2 | 6/2013 | Horvath | |
| 10,292,788 B2 | 5/2019 | Muller et al. | |
| 2004/0049099 A1* | 3/2004 | Ewers | A61B 17/3423 600/206 |
| 2004/0097795 A1* | 5/2004 | Horvath | A61C 5/90 600/237 |
| 2006/0223028 A1* | 10/2006 | Horvath | A61C 5/82 433/136 |
| 2017/0196659 A1* | 7/2017 | Muller | A61C 5/90 |

FOREIGN PATENT DOCUMENTS

DE            3329919 A1    4/1985

* cited by examiner

*Primary Examiner* — Eduardo C Robert
*Assistant Examiner* — Michelle C Eckman
(74) *Attorney, Agent, or Firm* — Ann M. Knab; Thad McMurray

(57) ABSTRACT

The inventive film clamping element (10) is held by a lip ring (14) and a vestibular ring (16), between which and possibly beyond which a film (12) extends. The film (12) and also the rings (14, 16) are elastically deformable, and it is provided that the film (12) comprises an attachment (24, 26) each at two positions opposite one another. Between these attachments (24, 26), at least one elastic band (20, 22) extends which is suitable to constrict the film (12) radially towards the inside.

22 Claims, 6 Drawing Sheets

FILM CLAMPING ELEMENT

CROSS-REFERENCE TO RELATED APPLICATIONS

This application claims priority to European patent application No. 18212089.9 filed on Dec. 12, 2018, the disclosure of which is incorporated herein by reference in its entirety.

TECHNICAL FIELD

The invention relates to a film clamping element.

BACKGROUND

Film clamping elements of this type have been known for a long time. By way of example, it is referred to in WO 03/51185 A1 and corresponding U.S. Pat. No. 7,988,626, which is hereby incorporated by reference. Film clamping elements of this type are to ensure free access to the mouth of the patient. For this purpose, an ovally or circularly disposed film is provided which extends between two rings which are referred to as lip ring and vestibular ring. The film may also be mounted slidably on one of the rings.

In any case, it is elastic and, in this respect, adjusts to the course of the lips of the patient and covers the lips at the same time.

Both the lip ring and the vestibular ring are comparatively stiff compared to the film element. Thus, they tension the film element between them, whereby the film element automatically widens the mouth of the patient.

The anatomic situation of the oral cavity and in particular of the vestibule and the lip area differ from one another significantly usually with regard to different patients. The elasticity of the film element is to account for this situation in the known solutions. In this case, the film extends from the vestibule of the patient over the constriction at the lips to the outside, wherein a comparatively large lip ring is to improve distribution of the occurring forces.

Particularly in the interior of the mouth, that is to say in the region of the vestibular ring, the tension introduced is frequently perceived as uncomfortable by the patient as the vestibular ring is frequently supported on the jaw bone of the patient.

Thus, it has become known from EP 3 160 381 A1 and corresponding U.S. Pat. No. 10,292,788, which is hereby incorporated by reference, to produce a pretension corset which accounts for the frenulum and thus reduces the introduced tension.

This represents considerable improvement compared to the original solution, but is basically still worthy of improvement.

A further problem of the film clamping elements used up to now is the pressure which is exerted on the lips and which differs quite considerably from patient to patient.

On the one hand, this pressure depends on the size of the two rings compared to the mouth opening of the patient, but on the other hand of course on the materials used.

Too great a pressure in particular on the jaw bones and the frenula is perceived as uncomfortable. On the other hand, the stretching function of the film clamping element depends considerably on the force acting radially towards the outside.

Thus, film clamping elements are typically kept in stock in several sizes to carry out adjustment to different anatomies of different patients.

As the film needs to be extremely elastic, a material suitable for this purpose such as an elastomer or soft silicone is frequently used.

SUMMARY

In contrast, the invention is based on the task of providing a film clamping element according to the claims, which allows for improved acceptance.

This task is inventively solved by the claims. Advantageous embodiments may be taken from the subclaims.

The inventive film clamping element is inventively characterized by a special elastic band which extends circularly around the film or along the film, namely in the region between the two rings, and which draws the film radially towards the inside thereat. Even though the elastic band should actually counteract the preventive function or else the function of pulling away of the film clamping element per se, in the inserted state the elastic band comes to rest either in the transition zone between the outside and the inside of the lip or on the inside of the lip.

In this way, it causes a tensile force on the vestibular ring and draws this ring away from the alveolar ridge and the labial frenula. In this respect, now the vestibular ring is in parallel contact with a site of the soft tissue of lips and cheeks which is not very sensitive to pressure in comparison.

That the elastic band extends slightly more along the vestibular ring than along the lip ring, is also because of their size ratio; typically, the diameter of the lip ring is, for instance, 10 or 20% larger than that of the vestibular ring.

Wearing comfort is improved considerably with the inventive film clamping element. The film is drawn towards the inside such that the vestibular ring is more prominent in the mouth which facilitates insertion of the film clamping element. The pressure on the jaw bone is smaller such that pain reactions are reduced which in the past have led to the vestibular ring being removed from the mouth of the patient and the upcoming operation being continued without auxiliary means.

Preferably, the inventive elastic band is mounted floatingly on the film. Preferably, it is fixed with one, further preferably with two attachments. The attachments extend from the vestibular ring along the film but in such a way that the elastic band is spaced apart from the vestibular ring also at this site.

The elastic band is elastic to such an extent that it may be pulled over a part of the vestibular ring. Either, a circular elastic band is provided, or two elastic bands are provided which complement one another to form a circle. In that case, every elastic band may be pulled over the associated part of the vestibular ring.

In fact, it is possible to attach the elastic band to any desired positions on the film element. The fixings may be realized for instance by means of two points between the film and the elastic band. However, it has proven to be particularly favorable to have two attachments opposite one another starting from the vestibular ring, and to attach them thereat by means of a welding spot on the film, for instance at a distance of approximately 1 cm from the vestibular ring.

However, it is also possible to attach the elastic band only to a part of the circle of the film, in which case the inventive effect takes place partially.

In an advantageous configuration of the invention it is provided that the elastic bands extend between the attachments in the state where they are not pulled over in a limp fashion or minimally tensioned, that is to say with considerably less than 10% of their maximum tension force.

In a further advantageous configuration of the invention it is provided that the elastic bands and the attachments are integral and/or consist of the same material.

At least the majority of the elastic band extends preferably radially outside of the film. Preferably, it may be pulled over a part of the vestibular ring and may be used to tension the film radially towards the inside. It is connected to the film and/or the vestibular ring and/or the lip ring at least one, preferably at least two connection sites.

The thickness and width of the elastic band may be adapted to the requirements to a large extent. For instance, it may have a circular, oval, square or rectangular cross-section or any other desired cross-section.

In case of a flat cross-section, that is to say a cross-section in which the thickness is smaller than the width, it clings to the film particularly easily.

Preferably, it lies flat against the outside of the film, namely particularly over considerably more than half of the ring extension of the film.

Its distance to the vestibular ring is smaller, for instance 1 mm to 15 mm, preferably at the position or positions at which it is connected with the film or a ring, and larger, up to half the distance between the rings or even more, at positions spaced apart therefrom, that is to say at positions which extend laterally when it is positioned in the mouth.

The elastic band may be pulled over the ring during production and may be delivered like this. Alternatively, it is also possible to ask the customer to pull it over the ring.

It is also possible to use a commercially available rubber band, for instance having a rectangular or square cross-section, and to connect it with the film and/or a ring at least at one position, preferably at the frenulum, and to cause it to extend all around the film.

The elastic band reduces the diameter of the film at the position at which it extends and gathers it.

In a further configuration it is provided to cause the cross-section and thus the tension force of the elastic band(s) to change over its/their course, and thus to simulate the anatomy of the lips.

For instance, in the lateral region, the tension force may be set to be larger, and smaller at the top and at the bottom.

In that case, the film is gathered more strongly laterally than at the top and at the bottom. This results in a flat-oval cross-section of the initially circular film clamping element, at least in the region of the film.

A precondition for this is to connect the elastic band with the film at several positions, in particular also laterally.

It is also possible to cause several elastic bands to extend all around the film next to one another in the side view. They may have the same elasticity and tension force, but if necessary also different tension forces.

For instance, an elastic band positioned in the middle may have the largest tension force, and the elastic bands extending between the elastic band positioned in the middle and one ring each have a smaller tension force each.

Preferably, the film is pretensioned automatically to have the shape of a lip or a shape similar to a lip, for instance by means of the above-mentioned multiple arrangement of elastic bands.

It is also possible to use a film material or a film-like material for the configuration of the elastic band(s). Such a band may have a thickness of between 0.05 and 1 mm and a width of between 3 and 8 mm. 0.3 mm*5 mm are preferred.

The band may also be laminated onto the film such that the connection runs around the entire circumference of the film, and the band is connected securely with the film.

It is also possible to configure the film as a layered film with several layers. In that case, one layer can form the elastic band, preferably in the shape of a ring, approximately centrally between the rings or slightly shifted towards the vestibular ring.

The elastic band may also be configured as a thickening of the film extending centrally between the rings. Because of its larger tension force it produces the inventive constriction.

When viewed in the transverse view, the profile of the film gets closer to the lip profile by means of the elastic band and its position, which also considerably facilitates introduction of the film clamping element into the oral cavity.

In this respect, a special advantage is provided in that insertability of the film clamping element with the inventive elastic band which causes the film to constrict is improved considerably.

According to the invention it is preferred that the elastic band may be pulled over a part of the vestibular ring. It is connected therewith preferably at two attachments but considerably more elastic compared thereto. In the relaxed state it is shorter than the circumference of the vestibular ring. However, due to its elasticity it may be moved over its outer circumference readily.

In order to activate the elastic band it is lifted without further ado, for instance using one or two fingers, and pulled over the respective part of the vestibular ring. This process may also take place at the factory and supported by machines.

In an advantageous configuration two elastic bands are provided which extend between opposite positions of the vestibular ring like limp tendons in the relaxed state. The film clamping element is produced in this form.

Two attachments extend from opposite positions of the vestibular ring towards one another, and every attachment ends in two ends of an elastic band, at the support base.

Preferably, it is provided that the connection site is between the vestibular ring and the support base.

Preferably, it is provided that the protrusion edge of the vestibular ring comprises a padding which is recessed at the tangential connection sites of the attachments.

In an advantageous configuration it is provided that the attachments are turned over and affixed to the film, for instance by laser welding, ultrasound welding, gluing or sewing or another joining process, approximately 0.5 cm to 12 mm away from the vestibular ring. In this way, the elastic band or elastic bands are tensioned. Still, the tension in the elastic band is so small that the respective elastic band cannot tear in any case.

For activation, the right elastic band is now turned or pulled over the right part of the vestibular ring and the left elastic band is turned or pulled over the left part.

Now, both elastic bands together form a circle which rests against the film from the outside and pretensions it radially towards the inside. Pretensioning takes place at a small distance from the vestibular ring, for instance at a distance of 1 cm, wherein the distance from the vestibular ring increases with increasing distance from the attachment, such that the elastic band slides towards the center between lip ring and vestibular ring thereat, that is to say into the position lowest in energy.

The film element, which has been pre-assembled limply, is pretensioned by the elastic band radially towards the inside at that position. On the other hand, it forms soft loops as there is excess material due to the smaller diameter now.

By the way, these loops have a damping effect and are downright comfortable on the sensitive skin of the lips as they are extremely elastic.

BRIEF DESCRIPTION OF THE DRAWINGS

Further advantages, details and features may be taken from the following description of several exemplary embodiments of the invention in conjunction with the drawings, in which.

DETAILED DESCRIPTION

Figure 1:
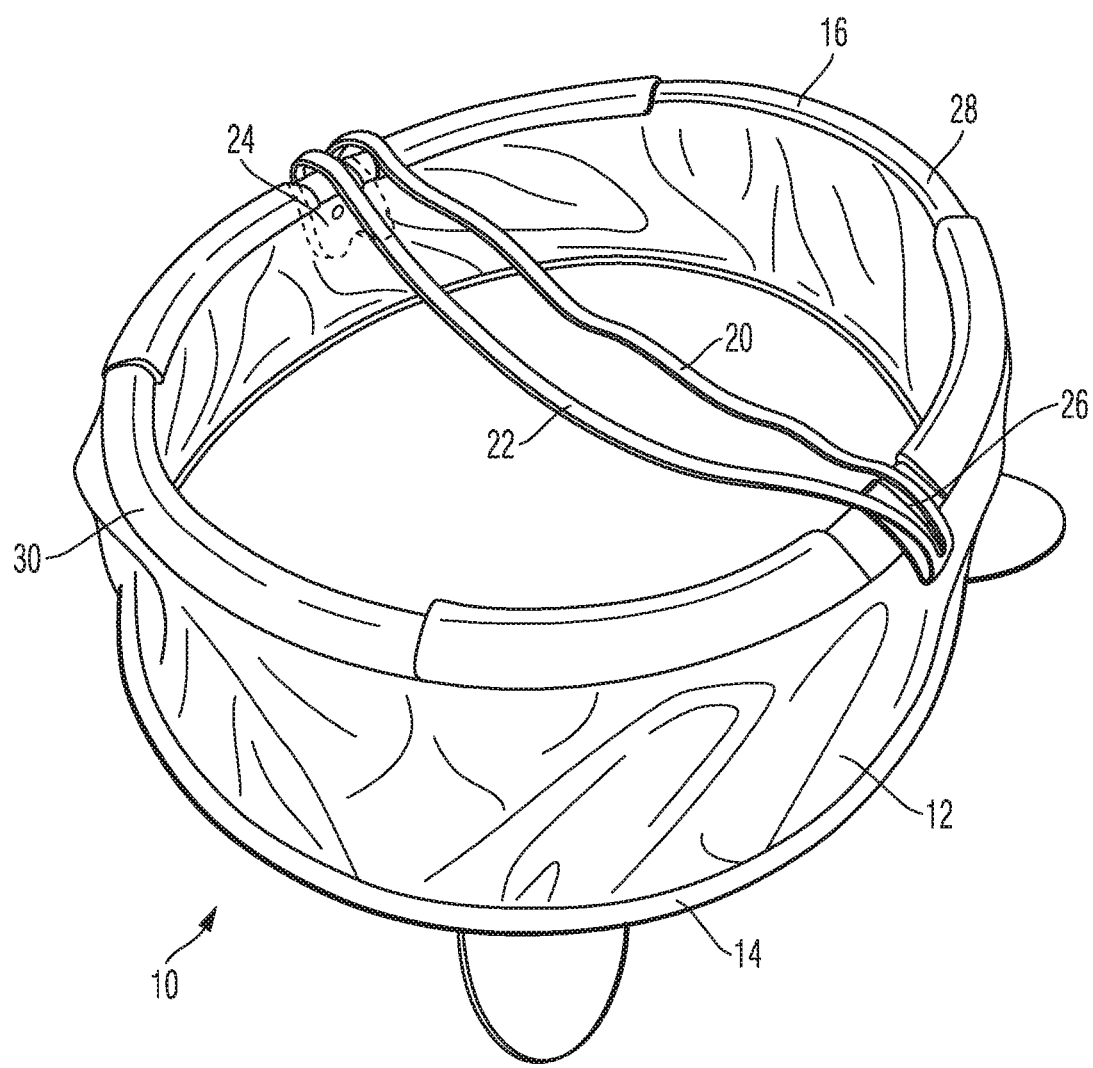
FIG. 1 shows a perspective view of an inventive film clamping element in one embodiment.

The film clamping element 10 illustrated in FIG. 1 comprises a film 12 which extends between a lip ring 14 and a vestibular ring 16. Both rings are stiff but still elastically deformable. The film extends practically in the shape of a ring or a jacket such that the interior both of the vestibular ring 16 and of the lip ring 14 is free from material.

In this exemplary embodiment, the lip ring 14 is slightly larger than the vestibular ring 16 in a way known per se.

At least one elastic band 20 extends transversely over the vestibular ring 16. In the exemplary embodiment illustrated, a further elastic band 22 is provided which extends parallel to the elastic band 20.

The bands 20 and 22 may also be spaced apart from one another considerably farther such that crescent-shaped constrictions are formed.

Both elastic bands are anchored at the attachments 24 and 26 wherein every elastic band 20 and 22 extends between these two attachments 24 and 26.

The attachments 24 and 26 are attached to the vestibular ring 16 for their part and additionally to the film 12 in the preferred exemplary embodiment illustrated.

Preferably, the elastic bands 20 and 22 are made of the same material as the film 12 and are highly elastic.

They are elastic to such an extent that it is possible without further ado to pull them over the respective adjacent part of the vestibular ring, that is to say the right elastic band 20 over the right part 28 and the left elastic band 22 over the left part 30 of the vestibular ring 16.

When both bands 20 and 22 are pulled over the vestibular ring 16, they substantially form a circle.

Figure 2:
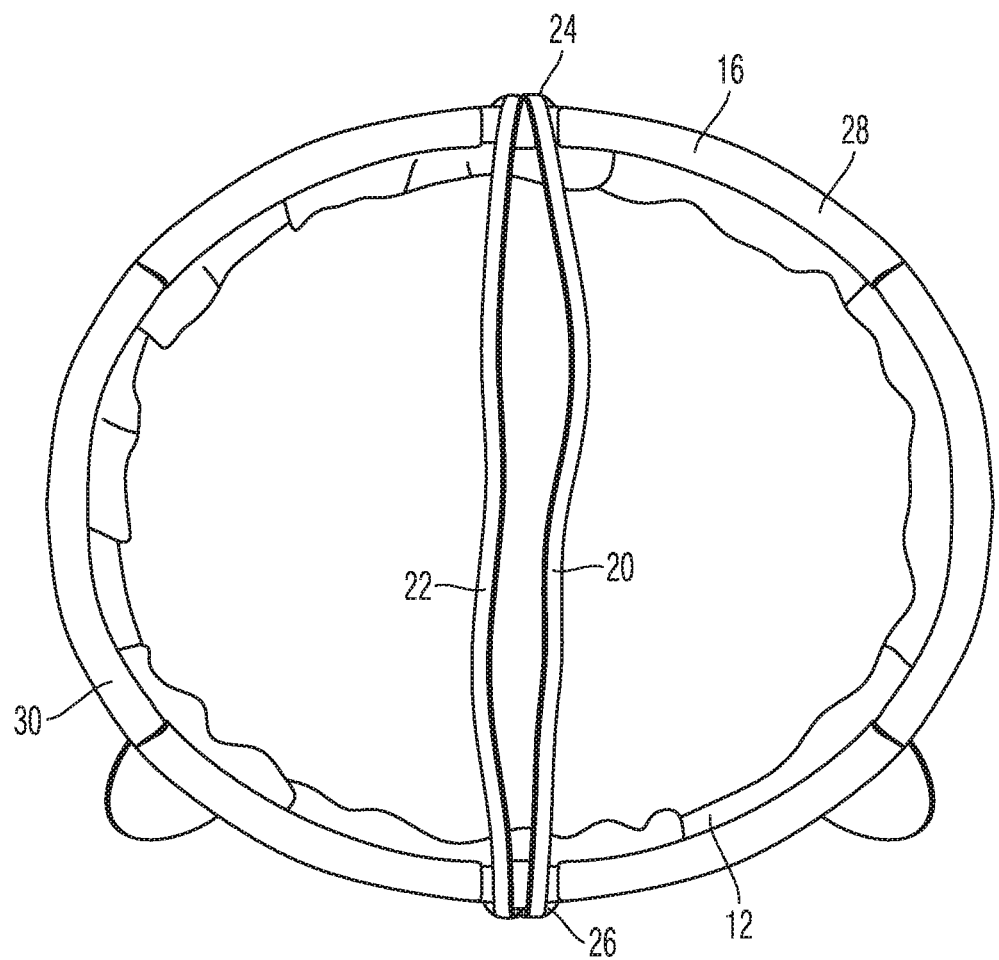
FIG. 2 shows the film clamping element according to FIG. 1 in the top view.
Figure 3:
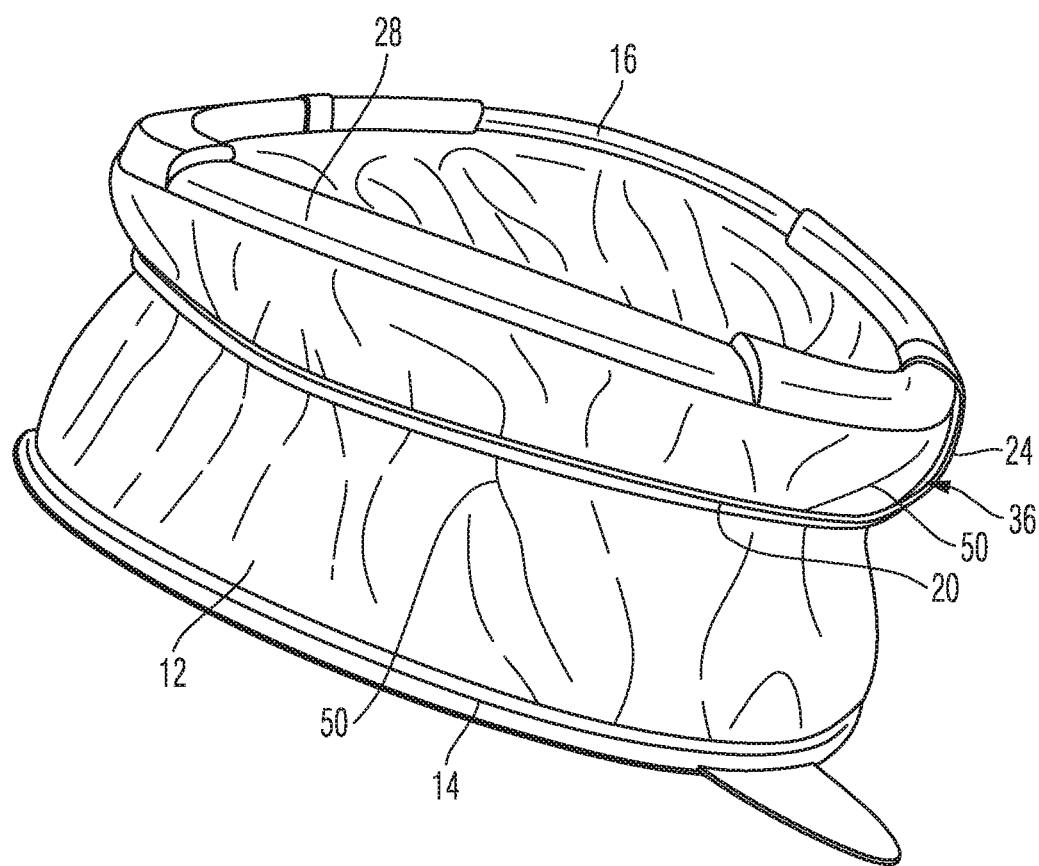
FIG. 3 shows the film clamping element according to FIGS. 1 and 2 but with an elastic band pulled over part of the vestibular ring.

It is apparent from FIG. 2 and FIG. 3 how the attachments 24 and 26 are configured. Every attachment is attached to the vestibular ring like a flap in such a way that both attachments 24 and 26 are opposite one another.

Additionally, every attachment extends radially outside of the film 12, partially beyond it.

The attachment 24 is connected with the film 12 at the position 36 by ultrasound welding, and the attachment 26 at the opposite position.

Figure 4:
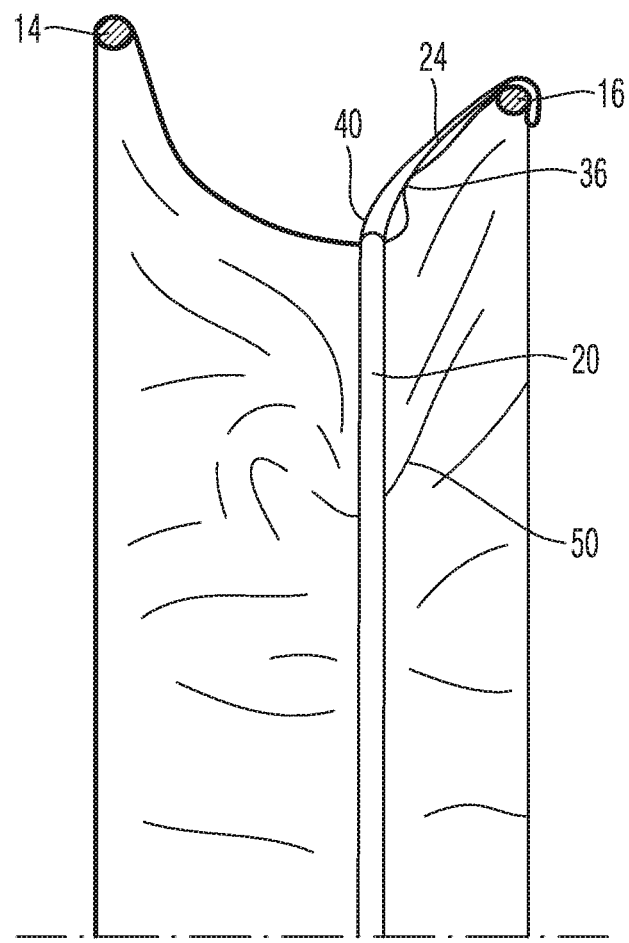
FIG. 4 shows an enlargement of a detail from FIG. 3.
Figure 5:
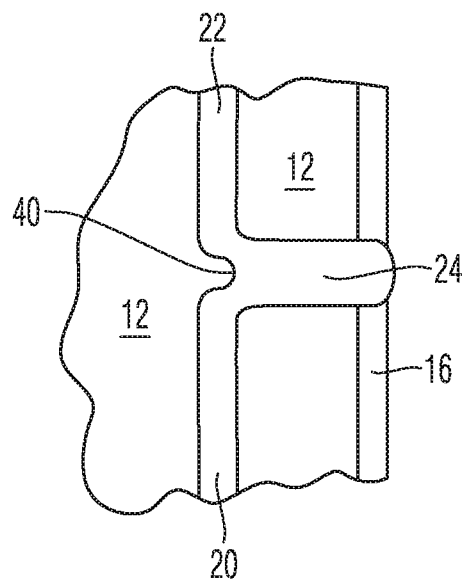
FIG. 5 shows a top view of a detail from FIG. 3.

These two positions are spaced apart from the vestibular ring considerably. However, the attachment 24 or 26, respectively, extends slightly beyond each considered position 36 as far as a support base 40 (FIG. 4). This support base 40 is located at the distal end of the attachment 24 or 26, respectively, and the elastic bands 20, 22 extend therefrom, namely divergent from one another (FIG. 5).

At this position the elastic bands 20, 22 are turned over in the position according to FIG. 2 and extend beyond the vestibular ring 16 over the open end of the film clamping element 10.

However, it is possible to tension both elastic bands 20 and 22 and to pull them over the vestibular ring 16. This state is illustrated in FIG. 3. In this state, the right elastic band 20 is pulled further to the right until it extends over the right part 28 of the vestibular ring 16. It is released just behind this part such that it contracts again and assumes approximately the shape according to FIG. 3.

In this shape, the elastic band 20 tensions the film 12 radially towards the inside. The position at which this happens is determined by the length of the attachments 24, 26, in particular by the position of the connection sites 36.

At this position, the film 20 forms loops 50 which have an additional damping effect.

The elastic band 20 automatically slides into the position lowest in energy, that is to say into the position in which the tension between lip ring 14, vestibular ring 16, film 12 and elastic band 20 keeps its balance.

This position illustrated in FIG. 3 is ideal for the best wearing comfort of the patient wherein reliable coverage of the mouth opening is provided nevertheless.

Figure 3A:
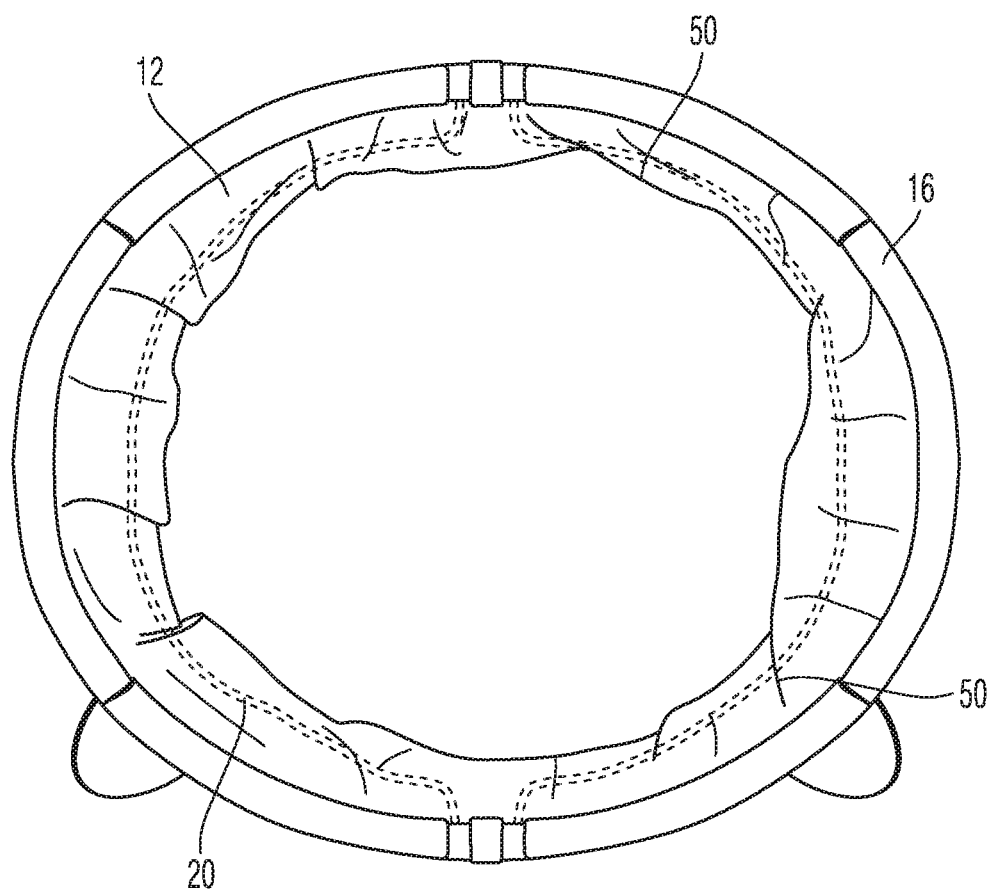
FIG. 3a shows the film clamping element according to FIGS. 1 and 2 but with an elastic band pulled over part of the vestibular ring.

As a consequence of the comparison of FIGS. 3a and 2, the film 12 has a smaller inside diameter radially and is pre-tensioned radially towards the inside when the elastic band 20 is activated.

The position of the elastic band 20 apparent from FIG. 3 is apparent in a detailed fashion from FIG. 4. The support base 40 is shifted slightly towards the lip ring 14 when viewed from the connection site 36 where the welding is made.

The elastic band 20 starts thereat and clings to the film 12 radially on the outside.

The length of the attachment 24 which defines the distance to the vestibular ring 16, and also the location of the connection sites 36 determine an exact position.

Alternatively, it would also be possible to realize guidance of the elastic band 20 starting from the lip ring 14 using a correspondingly longer attachment 24.

FIG. 5 illustrates the attachment 24 in the top view. The attachment 24 consists of the same material as the film 12 and the elastic bands 20 and 22. The support base 40 enables almost a circular shape of the ring formed by the elastic bands 20 and 22.

It is also apparent that the attachment 24 comprises approximately three times the width of the elastic bands 20 and 22. The elastic bands 20 and 22 preferably comprise a flat-oval cross-section such that they can cling to the film 12 easily.

Figure 6:
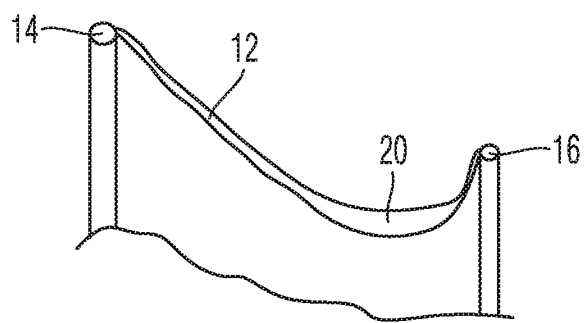
FIG. 6 shows a section of a detail of a further embodiment of the inventive film clamping element.

FIG. 6 shows a further embodiment of the invention. In case of this embodiment, the inventive elastic band 20 is integrated in the film 20. In this respect, it extends along the film as an annular thickening thereof along the entire circumference of the ring.

The thickening 20 has a greater tension force than the film 12 as for the rest. As a consequence, the film comprises a constriction at the position of the thickening 20 which extends in a way kind to the lips, that is to say which is similar to the bent circular shape of the lips.

When viewed from the outside and in section, the film forms a concave concavity with the elastic band 20 which envelops the lip gently and at the same time ensures that the vestibular ring is pulled away from the jaw bone.

The invention claimed is:

1. A film clamping element for dental treatments comprising
a lip ring (14) and
a vestibular ring (16), between which a film (12) extends, wherein said film (12) and said lip ring and vestibular ring are elastically deformable,
wherein the film (12) comprises an attachment (24, 26) at at least two positions opposite one another extending on an outside of the film, starting from which attachment at the at least two positions between which positions at least one elastic band (20, 22) extends which may be pulled over a part (28, 30) of the vestibular ring (16) and with which the film (12) may be tensioned radially towards the inside.

2. The film clamping element as claimed in claim 1, wherein the film (12) extends beyond the lip ring (14) and the vestibular ring (16).

3. The film clamping element as claimed in claim 1, wherein the film (12) and the at least one elastic bands (20, 22) are more elastic than the rings and have an E-modulus which is smaller compared to that of the rings by 80 to 99%.

4. The film clamping element as claimed in claim 1, wherein the at least one elastic band comprises two elastic bands (20, 22) which may be tensioned such that they complement one another to form a circle.

5. The film clamping element as claimed in claim 4, wherein each elastic band (20, 22) may be pulled over a part of the vestibular ring (16).

6. The film clamping element as claimed in claim 4, wherein each elastic band (20, 22) comprise approximately the same thickness as the attachment (24), and wherein the attachment comprises a width two to ten times a width of each elastic band (20).

7. The film clamping element as claimed in claim 4, wherein each elastic band thickness is ±30% thickness of a thickness of the attachment (24), and wherein the width of the attachment is three times the width of each elastic band.

8. The film clamping element as claimed in claim 1, wherein the attachment (24) extends away from the vestibular ring (16) along the film (12), and guides and supports the at least one elastic band (20, 22) at a support base (40) spaced apart from the vestibular ring (16) at a distal end of the vestibular ring.

9. The film clamping element as claimed in claim 1, wherein the attachment (24, 26) is molded to the film (12), and/or is fabricated of the same material, and wherein the attachment (24) extends over a fractional part of the distance between the lip ring (14) and the vestibular ring (16) over less than 60%.

10. The film clamping element as claimed in claim 9, wherein the attachment (24, 26) is molded to the film (12) integrally, and
wherein the attachment (24) extends over a fractional part of the distance between the lip ring (14) and the vestibular ring (16) over 10 to 45%.

11. The film clamping element as claimed in claim 9, wherein the attachment (24, 26) is molded to the film (12) integrally, and
wherein the attachment (24) extends over a fractional part of the distance between the lip ring (14) and the vestibular ring (16) over approximately 30%.

12. The film clamping element as claimed in claim 1, wherein the attachment (24) is connected or has been connected with the film (12) at a connection site (36) spaced apart from the vestibular ring (16).

13. The film clamping element as claimed in claim 1, wherein the at least one elastic band (20) comprises a flat or flat-oval cross-section with a width extending along the film (12).

14. The film clamping element as claimed in claim 1, wherein the at least one elastic band (20, 22) extends along the film element (10) on an outside and pretensions the film element radially towards an inside when the at least one elastic bands is pulled over the vestibular ring (16).

15. The film clamping element as claimed in claim 1, wherein the at least one elastic band (20, 22) pulls the film (12) further radially towards the inside at connection sites (36) spaced apart further from the attachments (24, 26) than at the attachments (24, 26) adjacent to the vestibular ring (16), when the at least one elastic bands is pulled over the vestibular ring (16).

16. The film clamping element as claimed in claim 1, wherein the at least one elastic band (20, 22) comprises a non-destructive elasticity of more than 1.2 times an initial length of the elastic bands.

17. The film clamping element as claimed in claim 16, wherein the elastic bands (20, 22) comprise a non-destructive elasticity of at least of twice the initial length or ten times to 50 times the initial length.

18. The film clamping element as claimed in claim 1, wherein the at least one elastic band comprises two elastic bands (20, 22) which are each supported on the same attachment (24) spaced apart from one another in the tangential direction of the rings by a few millimeters, and extend therefrom to the opposite attachment (26).

19. The film clamping element as claimed in claim 1, wherein a protrusion edge extends away from the film (12) in an extension thereof starting from the vestibular ring (16), and
wherein the attachments (24, 26) are attached to the protrusion edge.

20. The film clamping element as claimed in claim 1, wherein the at least one elastic bands (20, 22) contracts the film (12) radially towards the inside by 10 to 30% of a diameter and produces padding folds in the film element when the at least one elastic bands is pulled over the vestibular ring (16).

21. A film clamping element for dental treatments comprising
a lip ring (14) and
a vestibular ring (16), between and beyond the lip ring and vestibular ring a film (12) extends,
wherein said film (12) and said lip and vestibular rings are elastically deformable,
wherein at least one elastic band (20, 22) extends radially outside of the film (12), which elastic band may be pulled over a part (28, 30) of the vestibular ring (16) and with which the film (12) may be tensioned radially towards the inside and which is connected with the film (12) or one of the rings (14, 16) at at least two connection sites (36) positioned and extending on an outside of the film.

22. A film clamping element for dental treatments comprising
a lip ring (14) and
a vestibular ring (16), between and beyond the lip ring and vestibular ring a film (12) extends, wherein said film (12) and said lip and vestibular rings are elastically deformable, wherein at least one elastic band (20, 22) extends along the film (12), with which the film (12) may be tensioned radially towards the inside at a position between the rings (14, 16) and which is or may be connected with the film (12) or a ring (14, 16) at at least two connection sites (36) positioned and extending on an outside of the film.

\* \* \* \* \*